United States Patent [19]

Kuznetz

[11] Patent Number: 4,523,594
[45] Date of Patent: Jun. 18, 1985

[54] STRETCHABLE TEXTILE HEAT-EXCHANGE JACKET

[76] Inventor: Lawrence Kuznetz, 66 Joyce Rd., Plainview, N.Y.

[21] Appl. No.: 348,223

[22] Filed: Feb. 12, 1982

[51] Int. Cl.³ ............................................. A61F 7/00
[52] U.S. Cl. ..................................... 128/402; 128/399
[58] Field of Search .............................. 128/399–400, 128/402–403

[56] References Cited

U.S. PATENT DOCUMENTS

| | | | |
|---|---|---|---|
| 1,896,953 | 2/1933 | Hassell | 128/400 X |
| 1,970,200 | 8/1934 | Short | 128/399 X |
| 2,250,325 | 7/1941 | Barnes | 128/400 X |
| 2,397,232 | 3/1946 | Barnes et al. | 128/399 X |
| 3,079,765 | 3/1963 | Vantine | 128/402 X |
| 3,233,662 | 2/1966 | Yuen | 128/399 X |
| 3,744,555 | 7/1973 | Fletcher et al. | 128/402 X |
| 3,900,035 | 8/1975 | Welch et al. | 128/403 X |
| 3,995,621 | 12/1976 | Fletcher et al. | 128/402 X |
| 4,118,946 | 10/1978 | Tubin | 128/400 X |
| 4,149,541 | 4/1979 | Gammons et al. | 128/400 |
| 4,172,495 | 10/1979 | Zebuhr et al. | 128/402 X |
| 4,353,359 | 10/1982 | Milbauer | 128/402 X |

FOREIGN PATENT DOCUMENTS 2743919  4/1978  Fed. Rep. of Germany ...... 128/402

Primary Examiner—Lee S. Cohen
Assistant Examiner—Angela D. Sykes
Attorney, Agent, or Firm—Michael Ebert

[57] ABSTRACT

A stretchable textile heat-exchange jacket which wraps about and conforms to a limb, an arm or other body member and functions therapeutically to heat or cool the member. The jacket is formed by a sheet of elastic fabric material having threaded therein an array of flexible plastic pipes whose respective ends are coupled to an inlet fluid distributor and an outlet fluid collector. The sheet is provided at its opposing sides with complementary fabric fastener components to releasably hold the jacket securely in place on the body member even when the member is flexed. Fluid at a controlled temperature from a pressurized fluid source is fed into the inlet distributor, the fluid from the outlet collector being returned to the source for recirculation through the pipes.

7 Claims, 4 Drawing Figures

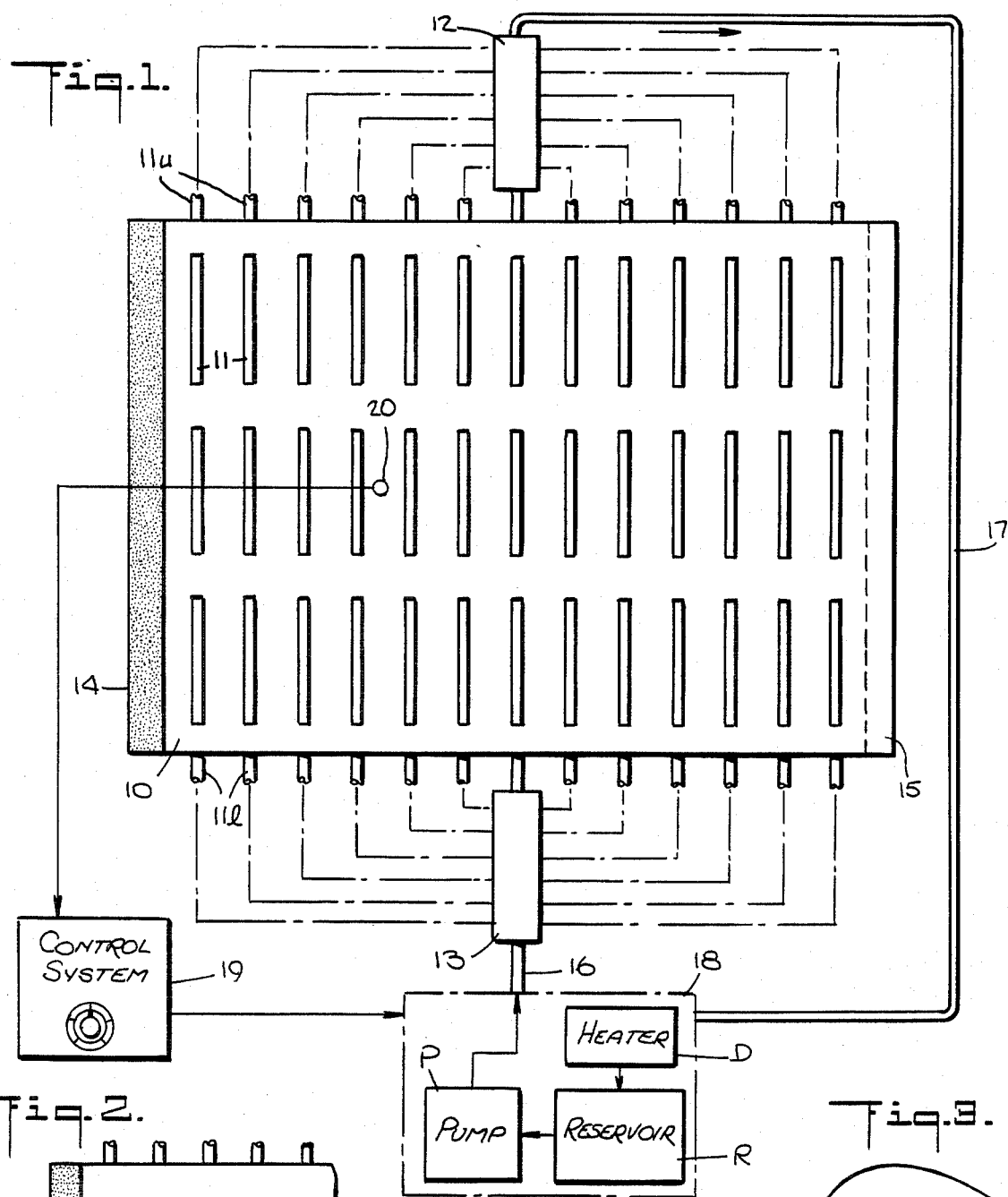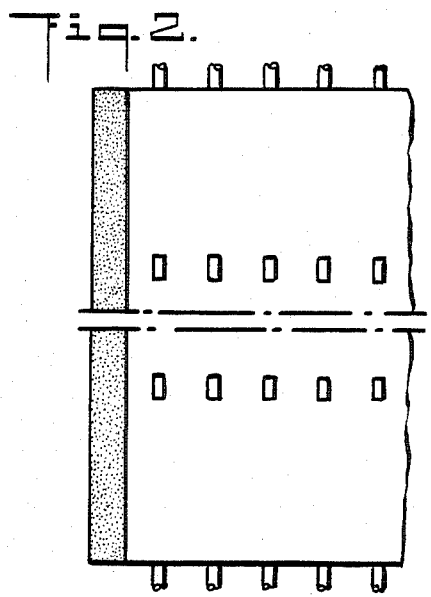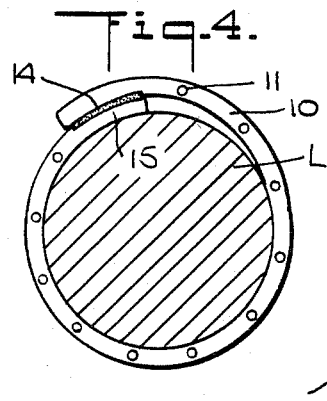

4,523,594

STRETCHABLE TEXTILE HEAT-EXCHANGE JACKET

BACKGROUND OF INVENTION

This invention relates generally to the application of a heating or cooling agent to limbs, arms and other body members for therapeutic purposes, and in particular to a stretchable textile heat-exchange jacket which is adapted to wrap about and conform to a body member, the jacket incorporating an array of flexible pipes through which a cold or hot fluid is circulated to cool or heat the body member at a controlled temperature level appropriate to the condition of the member.

Since ancient times, medical practitioners have known that the application of heat to the body is useful in the relief of muscle soreness and various aches and pains, as well as in the treatment of certain abnormalities. The use of heat in the treatment of arthritis and other abnormal conditions is commonplace. Heat is also employed medically in the resolution of infected areas. Also of therapeutic value in the treatment of particular conditions is the application of cold to an injured body member.

A typical thermal pack makes use of an absorbent blanket wrung out of cold or hot water, the moist blanket being then covered with a dry blanket before being wrapped about the patient's body. Such packs have limited utility, for the pack can only remain in a cold or hot state for a relatively brief period.

Another technique for creating a cold pack is to place ice cubes in a plastic bag and wrap the bag in a towel which is then applied to the site to be cooled. It has been reported in *Medical World News* (Aug. 3, 1981) that wrapping an arthritic knee in icepacks of this type several times a day constitutes a simple and effective way of managing pain in patients who have not been relieved by drugs. But, here again, since the ice in the pack melts, the pack has a limited effective life. Also, with a pack whose core is a cluster of ice cubes, the pack cannot be fully conformed to the member to be cooled; hence the cooling effect is uneven.

In some instances, as with athletic injuries, the prescribed treatment calls for alternative periods of heating and cooling, particularly for strained muscles, ligaments or sprains. Different types of injuries must be treated in ways appropriate to the injury. Thus joint injuries may benefit more from prolonged cold treatment, whereas muscle tears and capillary damage are best treated initially with a cold pack followed by elevated heat. Existing thermal treatment devices are either for hot or cold applications, and the same device cannot readily be switched from the one state to another. Thus one can fill a rubber bag with hot water to provide a heat pack; but if the bag is to be used for a cold application, one must replace the liquid.

Following knee, leg or other surgery on an extremity, there is usually swelling in the vicinity of the incision. When the wound is dressed in a surgical bandage, it becomes difficult to apply ice to the site to reduce swelling and promote healing. Moreover, since surgical bandages, casts and rubberized braces used during rehabilitation are relatively impermeable to perspiration and act as thermal barriers, there is often a build-up of moisture and heat under a surgical dressing. This may create a climate conducive to bacteria. Such bacterial activity may cause infection and retard the healing process. Another problem that is not relieved by conventional cold packs applied to the exterior of a cast or brace is the itching which often accompanies the healing process.

As noted in *The New York Times* of Apr. 14, 1981 (section C 2) in an article on modern approaches to cancer treatment, the application of heat to a body in a region containing a malignant tumor may cause this tumor to shrink and disappear. The effectiveness of heat therapy is based on the fact that cancerous tumors have poor circulation and a reduced ability to dissipate heat. "Thus a temperature of more than 113 degrees Fahrenheit would destroy cancer cells while sparing normal tissue." Yet existing heat packs or applicators are ill adapted to apply heat to a confined region at a predetermined temperature for a controllable period.

Heat is also of value when used in conjunction with chemotherapeutic agents delivered to the bloodstream during cancer treatment, for these agents may be administered more effectively if the tissues are heated and the blood vessels dilated in the region of concern. Here again, the need exists for a heat applicator capable of uniformly applying heat at a controlled temperature to a limited area of the body.

SUMMARY OF INVENTION

In view of the foregoing, the main object of this invention is to provide a stretchable textile heat-exchange jacket which can be wrapped about a knee or other body member for therapeutic heating or cooling purposes.

More particularly, an object of this invention is to provide a jacket of the above type which incorporates an array of flexible pipes through which a cold or hot fluid is circulated to uniformly cool or heat the body member embraced thereby.

A significant advantage of a textile heat-exchange jacket in accordance with the invention is that the jacket is thin and may be fitted under an existing surgical cast, bandage or braces without discomfort, whereby the jacket, when cold, serves to reduce swelling and arrest perspiration in the wound area and also acts to relieve post-operative itching.

Also an object of the invention is to provide a stretchable textile heat-exchange jacket which operates in conjunction with a pressurized fluid source which may selectively be rendered cold or hot to afford alternate cooling and heating actions, the temperature of the fluid being regulated to afford the desired therapeutic-temperature level.

Still another object of the invention is to provide a heat-exchange jacket that is relatively expensive to manufacture and yet is reusable, for the jacket is composed entirely of sterilizable material.

A salient feature of the invention is that the jacket, because it is stretchable and conforms to the body member, may be worn while the patient is performing exercises, making it possible to prescribe for a patient on an individual basis a heating-exercise regimen appropriate to his conditions. The need to exercise an injured member to prevent muscular atrophy is well known, but such exercise is often painful and difficult to carry out. By the use of a heat-exchange jacket in accordance with the invention, pain normally accompanying the exercise of an injured joint or other body member may be relieved.

Also an object of the invention is to provide a heat exchange jacket useful in hyperthermia and hypothermia medical procedures.

Briefly stated, these objects are accomplished by a stretchable textile heat-exchange jacket which wraps about and conforms to a limb, an arm or other body member and functions therapeutically to heat or cool the member. The jacket is formed by a sheet of elastic fabric material having threaded therein an array of flexible plastic pipes whose respective ends are coupled to an inlet fluid distributor and to an outlet fluid collector. The sheet is provided at its opposing sides with complementary fabric fastener components to releasably hold the jacket securely in place on the body member even when the member is flexed.

Fluid at a controlled temperature from a pressurized fluid source is fed into the inlet distributor, the fluid from the outlet collector being returned to the source for recirculation through the pipes.

OUTLINE OF DRAWINGS

For a better understanding of the invention as well as other objects and further features thereof, reference is made to the following detailed description to be read with the accompanying drawings, wherein:

FIG. 1 is a front view of a stretchable textile heat-exchange jacket in accordance with the invention, the jacket operating in conjunction with a pressurized fluid source;

FIG. 2 is a rear view of the jacket;

FIG. 3 is a perspective view of the jacket wrapped about the limb of an athlete; and FIG. 4 is a sectional view of the jacket wrapped about the limb.

DESCRIPTION OF INVENTION

Referring now to FIGS. 1 and 2, a stretchable textile heat-exchange jacket in accordance with the invention is shown, the jacket including a rectangular sheet 10 of fabric woven or otherwise fabricated of elastic cotton fibers, spandex or other natural or synthetic stretchable fabric material capable of being sterilized by conventional hospital procedures.

Threaded into the fabric sheet is a parallel array of flexible pipes 11 formed of synthetic plastic material such as "Tygon" tubing, Tygon being the U.S. Stoneware Co. trademark for a series of vinyl compounds. Use may also be made of polypropylene or other suitable soft and flexible plastic tubing. While pipes 11 are stitched into the fabric sheet, most of the tube surfaces are exposed and engage the body member when the jacket is wrapped thereabout.

Alternatively, the sheet may take the form of two superposed plies of open-mesh, stretchable fabric, with the pipes sandwiched therebetween in a manner in which the pipes form ducts between the plies.

The upper end portions $11_u$ of the pipes extend beyond the fabric sheet and terminate in a fluid outlet collector 12 so that all fluid passing through the pipes are collected by fluid collector 12 which forms a common outlet therefor. The lower end portion $11_l$ of the pipes extend beyond the fabric sheet and terminate in a fluid inlet distributor 13, so that fluid admitted into the distributor which acts as a manifold is dispersed to the several pipes in the array.

To releasably hold the jacket onto a body member such as a limb L (see FIGS. 3 and 4) about which the jacket is wrapped, a flexible fabric fastener is provided constituted by a male component in the form of a tape 14 ultrasonically or otherwise bonded to one side of the fabric sheet on the inner face thereof, and a female component in the form of a broader strip 15 bonded to the other side of the sheet on the outer face thereof.

The male component is constituted by a uniform dispersion of stiff nylon hooks, and the female component by a pile of tiny soft loops. When the components are pressed together, the hooks become embedded in the loops and held thereby until the components are peeled apart. Hook and loop fabric fasteners of this type are known commercially as "Velcro" fasteners. They are snag-proof, jam-proof, washable and sterilizable.

Velco fasteners are available in tape or strip form, the hook components being woven in the form of raised loops which are heat set to retain their shape, the loops then being cut to form hooks. The loop component is formed by a ground tape interwoven with a dense multiplicity of nylon yarns to form a pile surface that is then napped to create a continuous disoriented mass of uncut loops capable of engaging the male loops. Because the female strip is broader than the male tape, the jacket is capable of being wrapped about limbs of different diameter, for the fastening point is adjustable to the existing diameter.

A jacket in accordance with the invention may be made in a range of different sizes so that a jacket may be used for wrists, ankles, elbows, backs or any other body member, the jacket conforming itself to the body region of interest.

The heat-exchange jacket may be used in conjunction with a hot or cold pressurized water source in an open loop or a closed loop system. In an open loop system, the fluid supply line 16 coupled to fluid inlet distributor 13 is attached to the faucet of a house sink which then supplies tap water to the jacket, the water collected by outlet collector 12 and discharged through drain line 17 going back to the sink which acts as a sump. The hot and cold mixing valves of the faucet are adjusted to provide cold, warm or hot water flow through the jacket at a temperature appropriate to the treatment to be given. The open loop system is, of course, only feasible when the treatment can be given at a point close to an existing water faucet. Where, however, treatment is to be given in the field or at a site remote from a faucet, the need exists for a self-contained closed loop system.

In a closed loop system, a pressurized fluid source 18 is provided which is constituted by a small, electrically-operated water pump P installed in a reservoir R. The water in the reservoir is heated or cooled by a suitable thermoelectric device D of the type having a cold and a hot junction in an arrangement selectively controlled by an associated system 19 to provide either hot or cold water. The temperature of the hot or cold water is regulated by the control system 19 so that the water temperature is at a desired level. To this end, use is made of a temperature sensor 20 coupled to one of the pipes in the array to generate a signal whose magnitude is a function of the jacket water temperature.

Drain line 17 returns the water to supply 18 for recirculation through the array of pipes in the jacket. Thus if a water temperature of 35° F. is prescribed, the closed loop system will set and maintain the jacket temperature at substantially this level despite variations in ambient temperature, and the temperature of the body member.

Alternatively, the closed loop system may consist of a small water pump operating in conjunction with two reservoirs, the pump being coupled through a valve switch to either reservoir. One reservoir is filled with refrigerated water, the other containing hot water heated with an immersion heater or similar means, the switch making it possible to operate the jacket with either hot or cold fluid. In the closed loop system, the pump preferably operates in conjunction with a flow regulator to maintain a constant flow rate through the parallel pipes of the jacket.

A heat-exchange jacket in accordance with the invention has many uses. Thus a tool in the rehabilitation of athletes suffering from injuries, it may be placed over either a muscle region or joint that has sustained an injury. In modern sports medicine, a preferred method of treatment is to combine cold or heat and exercise in a prescribed manner. Immediately after an injury to a knee, the jacket is operated in the code mode for at least a half hour to reduce swelling and minimize pain. Pain is relieved because of the ice anaesthesia effect. Thereafter the jacket temperature is raised by running hot water through it while the knee is put through an exercise regimen. Because the jacket is stretchable, as the knee is flexed, the jacket will assume the same form.

The exercise program may be performed with Nautilus equipment, a stationary bicycle or whatever other equipment is indicated. The length and intensity of the exercise/heating cycle is determined on an individual basis, a one-half hour period for this purpose being typical.

Following the heat cycle, the jacket is then switched back to the cold mode. The alternate bouts of cold, heat and exercise cause a constriction and dilation of the blood vessels in the injured region which acts to purge or pump this area with an enhanced fresh blood supply to speed up the rehabilitation process.

Joint injuries may benefit from prolonged cold treatment, whereas muscle tears and capillary damage respond better to an initial cold treatment followed by operation of the jacket in the hot mode. Though the jacket will not rehabilitate structural damage, it will accelerate the healing process of injuries incurred during exercise that are non-structural in nature. If used properly under medical supervision, the jacket will function to speed recovery from surgery to correct structural damage.

The jacket is also usable as a training aid for professional athletes or serious amateurs. Frequently, athletic training programs such as those for marathon runners or basketball players are intensive to a degree giving rise to an elevated lactic acid level in the muscles. This lactic acid build-up causes fatigue and prevents complete muscle fiber recovery on a day-to-day basis, particularly when there is insufficient overnight rest to allow normal circulation to purge the lactic acid and other accumulated metabolites.

The heat-exchange jacket may therefore be used by athletes after strenuous workouts. By alternating cold, hot and exercise cycles in a manner calculated to increase local blood circulation, the removal of lactic acid and other metabolites can be facilitated to minimize fatigue and to promote muscle fiber recovery. In effect, this procedure affords the athlete the benefits of a good rest without actually taking a day off—thereby improving his performance.

While there has been shown and described a preferred embodiment of a stretchable textile heat-exchange jacket in accordance with the invention, it will be appreciated that many changes and modifications may be made therein without, however, departing from the essential spirit thereof.

I claim:

1. A heat-exchange system including stretchable textile heat-exchange jacket which is adapted to be wrapped about a body member such as a knee and which functions therapeutically to heat or cool the member embraced thereby, the system comprising:
   A. a stretchable fabric sheet having two sides, said fabric sheet being fabricated of elastic fibers and being provided with releasable means to hold the sheet in place to form a jacket when it is wrapped about a body member, whereby when the body member is bent the sheet assumes the same form;
   B. a parallel array of flexible pipes secured to the stretchable sheet whereby the sheet may then be stretched in a direction normal to the direction of the pipes, said pipes being in heat exchange relation to the body member and following the form assumed by the sheet, each pipe having an inlet end and an outlet end extending beyond said sheet; and
   C. means to conduct a fluid through the pipes in the array at a temperature level at which heat transfer takes place between the jacket and the member to effect the desired therapeutic action, said means including a source of pressurized fluid, a manifold distributor couple to the inlet ends of said pipes to supply fluid thereto in parallel paths, and a manifold collector coupled to the outlet ends of the pipes to collect the fluid therefrom, said distributor and said collector being external to said fabric sheet; said jacket being included in a closed loop system having said pressurized fluid source whose output is coupled to said distributor, the collector being coupled to the input of the source whereby the fluid recirculates in parallel paths through the pipes.

2. A system as set forth in claim 1, in which the sheet is fabricated of spandex fibers.

3. A system as set forth in claim 1, in which the pipes are formed of vinyl tubes which are threaded through the sheet.

4. A system as set forth in claim 1, in which the releasable means is formed by a fabric fastener having a male component in tape form bonded to one side of the sheet and a female component in strip form bonded to the other side of the sheet, the two components being joined when pressed together.

5. A system as set forth in claim 1, wherein said source includes a liquid reservoir associated with a thermoelectric element to heat or cool the liquid therein, and a pump to draw liquid from the reservoir and feed it into the manifold distributor.

6. A system as set forth in claim 5, further including a control system coupled to the thermoelectric element and to a temperature detecting sensor, said control system being responsive to the signal from the sensor, said sensor being coupled to a jacket pipe to maintain the jacket temperature at a pre-set level.

7. A system as set forth in claim 1, wherein said sheet is formed of two superposed plies of open-mesh, stretchable fabric and said pipes are sandwiched therebetween.

* * * * *

UNITED STATES PATENT OFFICE
CERTIFICATE OF CORRECTION

Patent No. 4,523,594                    Dated  June 18, 1985

Inventor(s) Lawrence Kuznetz

It is certified that error appears in the above-identified patent and that said Letters Patent are hereby corrected as shown below:

Column 6, line 27, after "fluid, a" insert -- manifold--; delete "mainfold".

Column 6, line 28, after "distributor" insert -- coupled -- delete "couple".

Signed and Sealed this

Eleventh Day of March 1986

[SEAL]

Attest:

DONALD J. QUIGG

Attesting Officer            Commissioner of Patents and Trademarks